United States Patent
Müller et al.

[11] Patent Number: 5,875,928
[45] Date of Patent: Mar. 2, 1999

[54] DEVICE FOR MIXING AND DISCHARGING A MOLDING COMPOSITION

[75] Inventors: Hans-Helmut Müller, Köln; Reiner Diederich, Wesseling; Otto Mengel, Köln; Alfred von Schuckmann, Kevelaer, all of Germany

[73] Assignee: Bayer Aktiengesellschaft, Leverkusen, Germany

[21] Appl. No.: 583,684

[22] Filed: Jan. 5, 1996

[30] Foreign Application Priority Data

Jan. 13, 1995 [DE] Germany .................. 195 00 782.4

[51] Int. Cl.[6] ............................... B67D 5/42; B67D 5/52
[52] U.S. Cl. .................. 222/82; 222/137; 222/145.6; 222/327
[58] Field of Search ................... 222/82, 137, 145.6, 222/183, 326, 327

[56] References Cited

U.S. PATENT DOCUMENTS

| | | | |
|---|---|---|---|
| 1,709,445 | 4/1929 | Tomes | 222/327 X |
| 2,587,683 | 3/1952 | Barry | 222/327 X |
| 2,692,706 | 10/1954 | Wiksten | 222/326 |
| 2,833,450 | 5/1958 | Sherbondy | 222/327 |
| 3,130,872 | 4/1964 | Myers et al. | 222/327 X |
| 3,311,265 | 3/1967 | Creighton, Jr. et al. | 222/137 |
| 3,390,814 | 7/1968 | Creighton, Jr. et al. | 222/137 |
| 3,570,719 | 3/1971 | Schiff | 222/137 |
| 3,658,213 | 4/1972 | Plumer | 222/327 X |
| 3,767,085 | 10/1973 | Cannon et al. | 222/137 X |
| 4,538,920 | 9/1985 | Drake | 222/137 X |
| 4,566,610 | 1/1986 | Herb | 222/327 X |
| 4,767,026 | 8/1988 | Keller et al. | 222/137 |
| 4,871,090 | 10/1989 | Hoffmann | 222/137 X |
| 5,033,650 | 7/1991 | Colin et al. | |
| 5,104,005 | 4/1992 | Schneider, Jr. et al. | 222/137 |
| 5,249,709 | 10/1993 | Duckworth et al. | 222/137 |
| 5,477,987 | 12/1995 | Keller | 222/137 |

FOREIGN PATENT DOCUMENTS

| | | |
|---|---|---|
| 0621083 | 10/1994 | European Pat. Off. . |
| 2806090 | 8/1979 | Germany . |
| 3412222 | 10/1985 | Germany . |
| 3501331 | 7/1986 | Germany . |
| 3738960 | 5/1989 | Germany . |
| 4026685 | 2/1992 | Germany . |
| 9306940 | 4/1993 | WIPO . |

*Primary Examiner*—Kevin P. Shaver
*Attorney, Agent, or Firm*—Sprung Kramer Schaefer & Briscoe

[57] ABSTRACT

The device for mixing and discharging a self-curing two-component molding composition comprises a two-plunger mixing gun having a gun body 1 and a receiving shaft 4 for 2 cartridges 11a, 11b filled with the individual components of the molding composition, and a static mixer 6 adjoining the receiving shaft 4 and with an outlet nozzle 7. In this arrangement, the cartridges 11a, 11b comprise separate cardboard sleeves 22, which are respectively provided with a terminating plate 23 and a plunger element 24. The cardboard sleeves are introduced into the receiving shaft 4, which can be closed by a pressure-resistant cartridge housing 5 enclosing the cardboard sleeves 22 flush with them. Also provided between the static mixer 6 and the cardboard sleeves 22 is a head piece 16, which can be inserted into the receiving shaft 4 and has separate flow channels 28a, 28b which are open towards the cardboard sleeves 22 and merge directly at the inlet into the static mixer 6.

5 Claims, 5 Drawing Sheets

DEVICE FOR MIXING AND DISCHARGING A MOLDING COMPOSITION

The invention is based on a device for mixing and discharging a self-curing two-component molding composition. The main component parts of this device are a two-plunger mixing gun having a gun body and a receiving shaft for two cartridges, which are filled with the individual components of the two-component moulding compositions, and a static mixer, which adjoins the receiving shaft and has an outlet nozzle. Such two-component discharge devices are described, for example, in EP 121,342 and EP 232,733. Main fields of application of these discharge devices are the unproblematical and clean handling of two-pack adhesives, jointing fillers and insulating foams. Furthermore, mixing systems of this type are used for the clean and ergonomic preparation of dental impression materials in dental practice. For this purpose, the two components of the impression composition which are to be mixed with each other are supplied in so-called two-component polymer cartridges. These double cartridges are placed into the mixing gun and arrested. By actuating the gun grip, a double plunger is actuated, which simultaneously forces out the components situated in the two cartridge cylinders and delivers them into a static mixer fitted onto the front end. The two-component mixture then leaves via a nozzle at the end of the mixer and can be applied in this form. After emptying, the polymer double cartridge, including closure, is discarded as waste and must be disposed of. In the case of this mixing system, particularly simple and operationally reliable handling are prime objectives.

Against this background, the invention is based on the object of developing an inexpensive, environmentally friendly and waste-optimized mixing system for two-component materials.

On the basis of the device described at the beginning for mixing and discharging a self-curing two-component molding composition, this object is achieved according to the invention a) in that the cartridges comprise separate cardboard sleeves, which are respectively provided with a terminating plate and a plunger element b) in that the receiving shaft can be closed by a pressure-resistant cartridge housing enclosing the cardboard sleeves and flush with them and c) in that there is provided a head piece, which can be inserted between the static mixer and the cardboard sleeves into the receiving shaft and has separate flow channels which are open towards the cardboard sleeves and merge directly at the inlet into the static mixer.

There is advantageously attached on the mixing gun body a coupling clip which locks the gun body frictionally with the cartridge housing as the cartridge housing is closed.

The cartridge housing is preferably fastened such that it can swivel on the receiving shaft with the aid of hinges and can consequently be swung open or shut in a simple way.

A further preferred embodiment consists in that the cardboard sleeves are provided with pierceable terminating plates and in that, for piercing the terminating plates, hollow spikes connected to the flow channels in the head piece and oriented with their tips towards the cardboard sleeves are attached.

For reasons of storage stability, the cardboard sleeves are expediently laminated on their inside with a film resistant to the individual components of the two-component molding composition.

The following advantages are achieved with the invention:

1. For the manufacturer
   a) considerable savings can be achieved in packaging costs and disposal costs;
   b) it is quite possible to operate with variable quantities filled into the cardboard sleeves;
   c) the production costs can likewise be reduced, since individual filling of the cartridges is possible and the expensive filling machines necessary for synchronous filling are no longer required.
2. For the user
   a) the invention provides a refillable mixing system;
   b) already existing mixing guns can be readily retrofitted with the device according to the invention;
   c) in dental practice, a considerable reduction in waste can be achieved;
   d) the novel mixing system likewise offers simple and clean handling;
   f) most of the parts of the mixing system are reusable; it is quite possible for the cardboard sleeves to be partly emptied;
   g) the cardboard sleeves provide a pack which is resistant to breakage, allowing damage during handling or during transport to be minimized.

The invention is explained in more detail below with reference to an exemplary embodiment represented in the drawing, in which.

Figure 1:
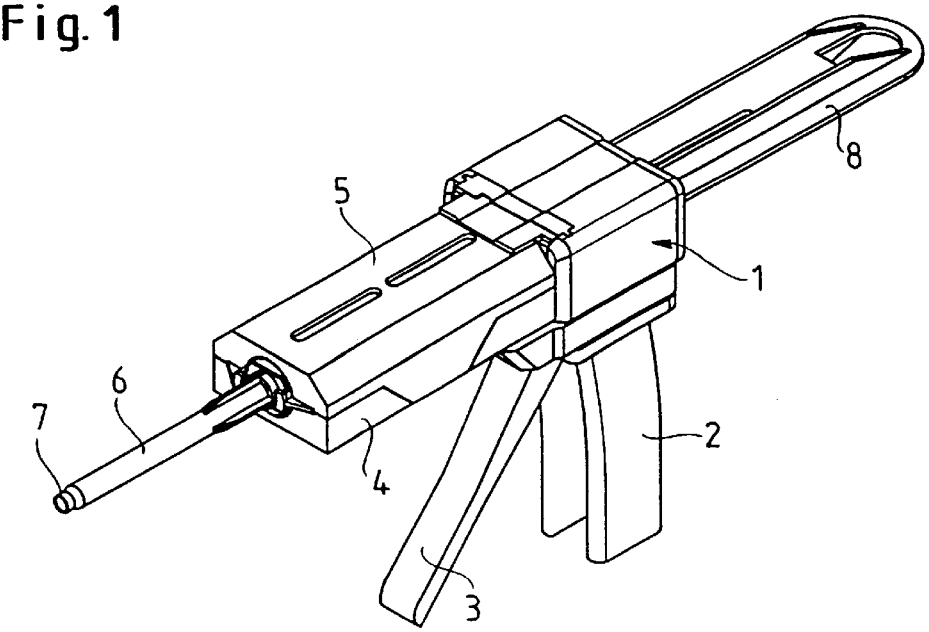
FIG. 1 shows the complete assembled two-component mixing gun in a perspective representation.

The two-plunger mixing gun according to FIG. 1 comprises a gun body 1 having a fixed grip 2 and a trigger lever 3, a housing 4 with a housing cover 5, a static mixer 6 fitted onto the receiving shaft 4 and with an outlet nozzle 7, and also a double-plunger rod 8 protruding out of the gun body 1. The receiving shaft 4 is securely connected to the gun body 1.

Figure 2:
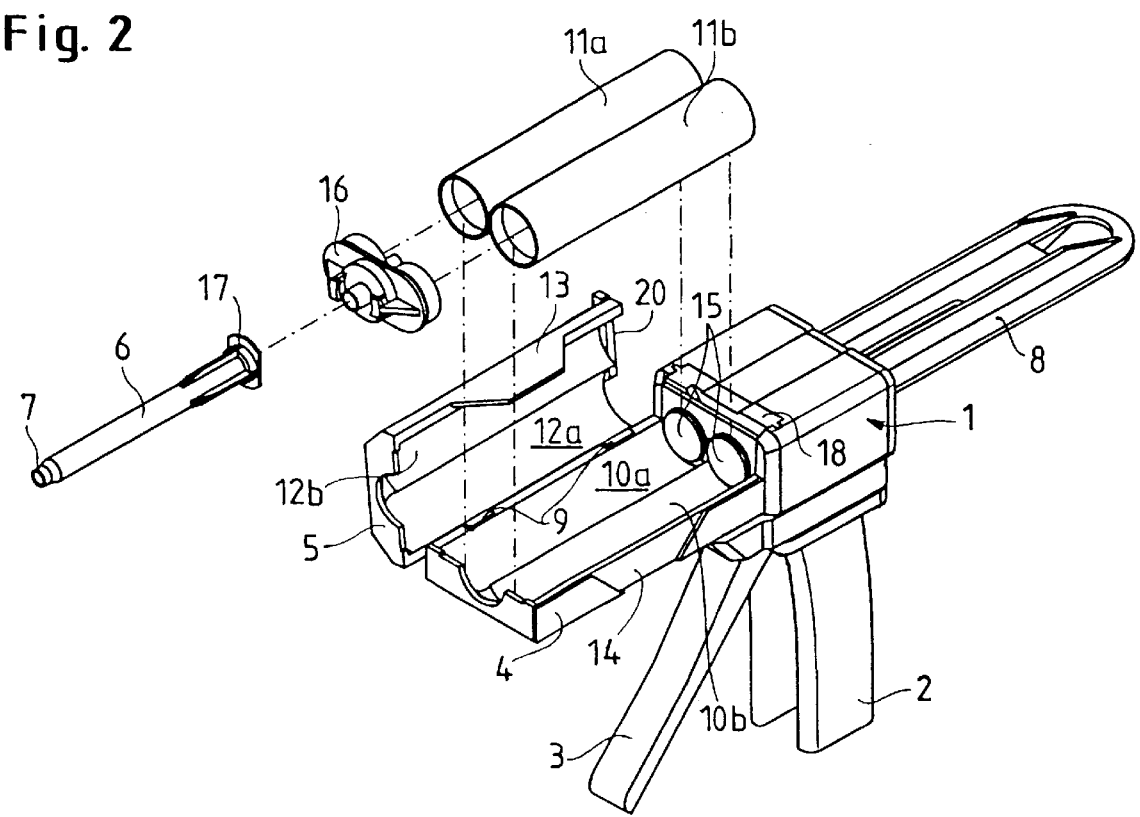
FIG. 2 shows an exploded drawing of the two-plunger mixing gun in a perspective representation.

FIG. 2 reveals that the cartridge housing is fastened to the housing 4 by means of the hinges 9 and can be swung open or shut. Provided in the receiving shaft 4 are semicylindrical recesses 10a and 10b for receiving individual cartridges 11a and 11b. The housing cover 5 also has similar semicylindrical recesses 12a and 12b, with the result that the cartridges 11a and 11b are frictionally and securely enclosed by the receiving shaft 4 and the housing cover 5 when the housing cover 5 is swung shut. The housing cover 5 also has a trapezoidal clip 13, which can engage in a correspondingly shaped recess 14 on the housing 4 and forms a snap closure. Attached on the front end of the double-plunger rod 8 are the plungers 15, which are introduced into the individual cartridges 11a and 11b when the plunger rod 8 is advanced. The semicylindrical recesses 10a, 10b in the housing 4 and 12a, 12b in the housing cover 5 are matched in their diameter to the outside diameter of the individual cartridges 11a, 11b such that the cartridges border flush with their surface against the inner surfaces of the recesses. In this way, the high pressure exerted on the content of the cartridges upon advancing of the plungers 15 is absorbed by the receiving shaft 4 and the housing cover 5. The advancing of the plungers 15 is performed by a prior-art rack-and-pinion drive (not shown) coupled to the trigger lever 3.

Provided between the static mixer 6 and the individual cartridges 11a and 11b is a head piece 16 which can be inserted into the receiving shaft 4. The head piece 16 forms the connecting piece between the individual cartridges 11a and 11b and the static mixer 6 and is described in still more detail further below. The static mixer 6 can be fastened on the head piece 16 by means of a plug-in flange 17.

Figure 3:
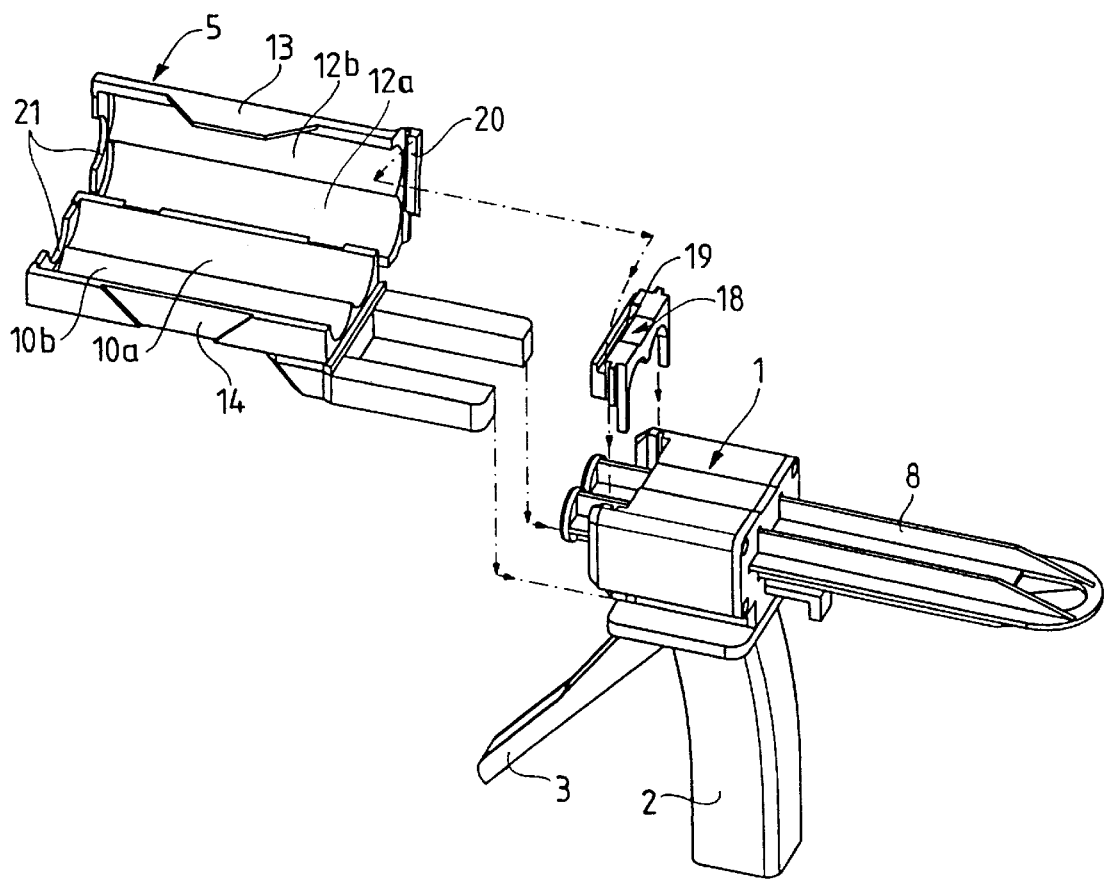
FIG. 3 shows a further exploded drawing of the two-component mixing gun with receiving shaft and cartridge housing and the coupling clip for connection of the cartridge housing to the gun body.

In FIG. 3 there is represented the housing 4 with the housing cover 5 in combination with a coupling clip 18 for the frictional connection of the housing cover 5 to the gun body 1 (in the form of an exploded drawing). The coupling clip 18 can be pushed into a corresponding recess on the gun body 1 and is then securely connected to the gun body. The coupling clip 18 has a transverse groove 19, which is designed such that a hook-shaped bow 20 on the housing cover 5 engages into the groove 19 when the housing cover 5 is swung shut. In this way, the gun body 1 is frictionally locked with the housing cover 5 as the cartridge housing 5 is closed. To be able to attach the mixer 6 (see FIG. 2) onto the head piece 16, semicircular complementary openings 21 are provided on the housing 4 and on the cover housing 5.

Figure 4:
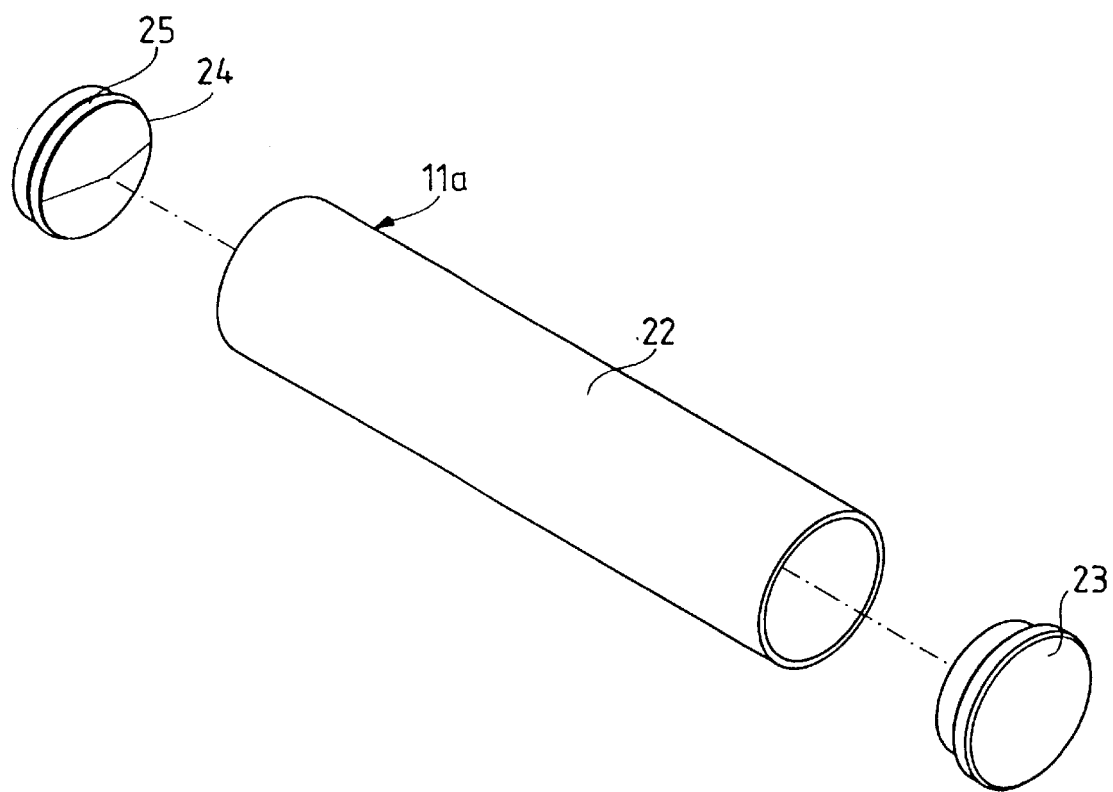
FIG. 4 shows a perspective exploded drawing of a cardboard sleeve with terminating cover and plunger.

The individual cartridge 11a or 11b, represented in FIG. 4, comprises a cylindrical cardboard sleeve 22 with a terminating cover 23 and a plunger plate 24. The plunger plate 24 is provided with an O-ring seal 25 or with moulded-on sealing lips, terminates flush with the inside wall of the cardboard sleeve 22 and, upon actuation of the trigger lever 3 and corresponding advancing of the plungers 15 (see FIG. 2), is pushed through the cardboard sleeve 22. The wall thickness of the cardboard sleeve 22 is 0.8 to 1.8 mm. On its inside, the cardboard sleeve 22 is laminated with a film resistant to the individual components of the two-component moulding composition. The lamination may comprise a parchment, aluminium or polypropylene film.

Instead of a terminating cover 23, a film closure may also be provided for the cardboard sleeve 22; i.e. the opening on the side opposite the plunger plate 25 is then closed by a film.

Figure 5:
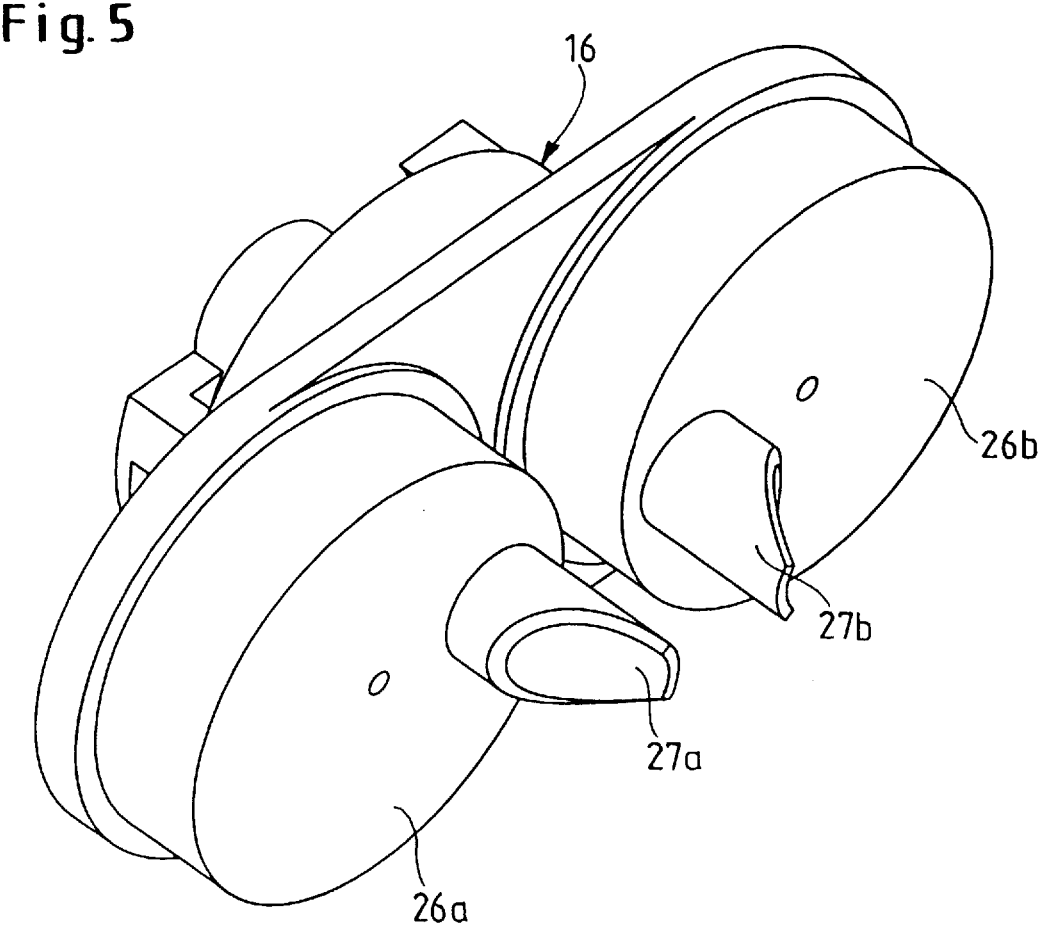
FIG. 5 shows a perspective representation of the head piece which can be inserted into the receiving shaft for the connection of the static mixer.
Figure 6:
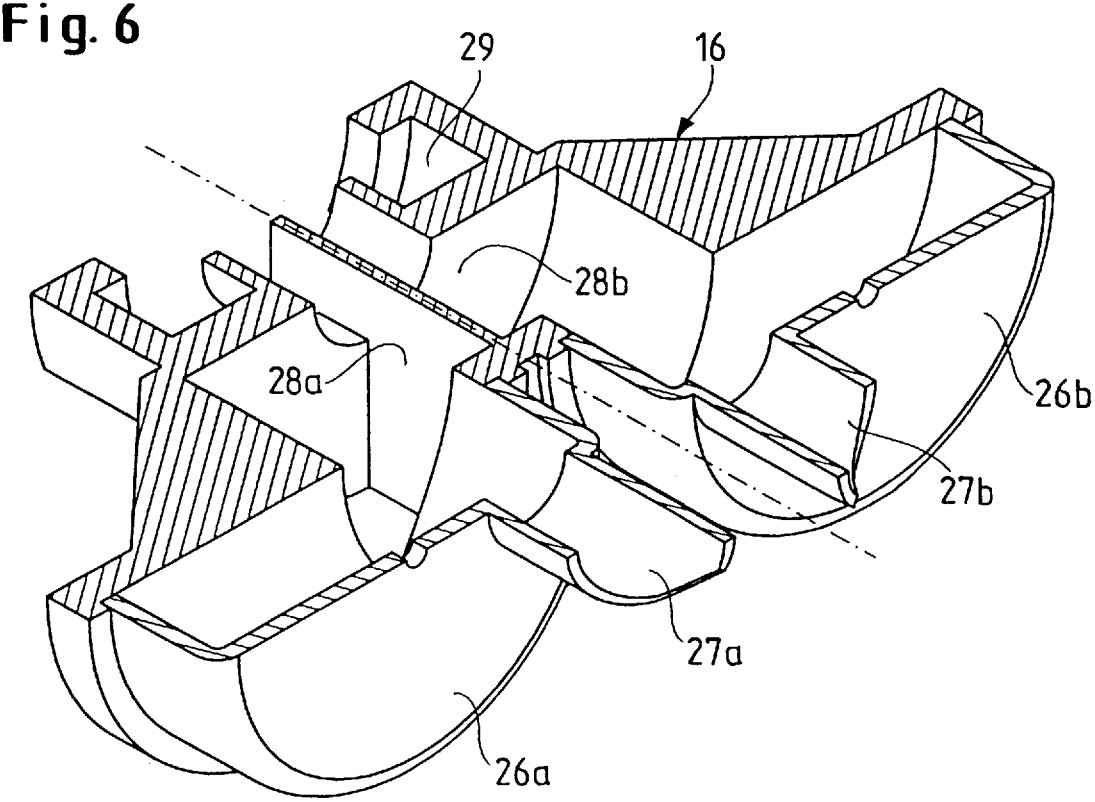
FIG. 6 shows a perspective sectional drawing of the head piece.

In FIGS. 5 and 6 there is represented the head piece 16 (cf. FIG. 2), which connects the individual cartridges 11a and 11b, comprising the cardboard sleeves 22, to the static mixer 6. For this reason, the head piece may also be referred to as a dual adaptor. The head piece 16 (dual adaptor) has two circularcylindrical continuations 26a, 26b, the diameter of which is adapted to the inside diameter of the cardboard sleeves 22. Moulded onto the cylindrical continuations 26a, 26b are hollow spikes 27a, 27b. If the cardboard sleeves 22 are closed by a film, as described above, this film is pierced by the hollow spikes 27a, 27b when the head piece 16 is inserted into the receiving shaft 4, and the cylindrical continuations 26a and 26b on the head piece form the termination of the cardboard sleeves 22. The dual adaptor 16 also provides for the secure holding-together of the cardboard sleeves 22 filled with the individual components. When inserting the dual adaptor, first of all the two cardboard sleeves are sealed off by the cylindrical continuations 26a and 26b. Upon further mechanical pressure, the film closures opposite the hollow spikes 27a, 27b on the cardboard sleeves are pierced, with the result that the pasty individual products situated in the cardboard sleeves can enter into the hollow spikes 27a, 27b. The two individual cartridges 11a, 11b, comprising the cardboard sleeves, are mechanically arrested by the dual adaptor 16. On the side opposite the hollow spikes 27a, 27b, commercially available static mixers 6 can be fitted onto the dual adaptor 16. For this purpose, the plug-in flange connection 17 is provided on the static mixer 6. An important feature of the dual adaptor 16 is the separate product passage from the cardboard sleeves 22 up to entry into the static mixer 6. For this purpose, there are machined into the head piece 16 separate flow channels 28a, 28b, connected to the hollow spikes 27a, 27b (see FIG. 6). This ensures that the individual components cannot mix with each other before entry into the static mixer 6. Also indicated in FIG. 6 is the flange recess 29 belonging to the flange connection 17 on the static mixer 6 (see FIG. 2).

The following is intended to describe once again in summary the function of the two-plunger mixing gun. The cardboard sleeves 22 filled with the individual components and still closed (terminating cover 23 or equivalent film closures) are first of all placed into the receiving shaft 4. Subsequently, the head piece or the dual adaptor 16 is inserted into the receiving shaft 4 and pressed against the individual cartridges 11a, 11b, comprising the cardboard sleeves 22 (see FIG. 2). When this happens, the film closure is opened, as described above. Thereafter, the cartridge housing 5 is swung shut and is closed. Subsequently, the static mixer 6 can be fitted by means of the flange connection 17 onto the front part of the head piece 16 protruding out of the receiving shaft 4 or the cartridge housing 5. The device is then ready to operate. After discharging the entire content of the cartridges, i.e. when the cardboard sleeve cartridges 11a, 11b are empty, the receiving shaft 4 is again fitted with new filled individual cartridges.

We claim:

1. A two-plunger mixing gun for forming and dispensing a self-curing two-component molding composition, comprising a body (1) having a fixed grip (2), a trigger lever (3), a cartridge housing (4) and cartridge housing cover (5), said cartridge housing having a first end and a second end, said cartridge housing and housing cover having complementary semi-cylindrical recesses (10a, 10b, 12a and 12b); two plunger rods (8) each having a first end which protrudes out of the body (1), and a second end which is provided with a plunger (15) and movable, by actuation of said trigger lever, into the first end of said cartridge housing; a head piece (16) which is removably inserted into said housing adjacent the second end of said cartridge housing, a first side of said head piece facing said cartridge housing, and a second side of said head piece facing away from said cartridge housing, said first side of said head piece having two cylindrical continuations (26a, 26b) having hollow spikes (27a, 27b) molded therein, said hollow spikes communicating with separate flow channels (28a, 28b) molded internally in said head piece, said second side of said head piece having flange recesses (29) for connection of a static mixer thereto, and an inlet for a static mixer; said internal flow channels merging into said inlet; and a static mixer (6) having an inlet end and an outlet end, with flange connections (17) at the inlet end, which are attachable to said flange recesses (29) and an outlet nozzle 7 at said outlet end, whereby in operation, individual cartridges (22), each containing one of said two components, are inserted into said cartridge housing (4), cartridge housing cover (5) is closed; trigger lever (3) is actuated to cause said plungers to move against said cartridges and force said cartridges against said head piece and said spikes (27a, 27b) whereupon said spikes pierce said cartridges so that the components contained within said cartridges are forced into said flow channels (28a, 28b), and to flow through said flow channels into said static mixer inlet and through said static mixer, where they are mixed to form said two-component composition, which is then discharged through said outlet nozzle.

2. The two-plunger mixing gun according to claim 1, further comprising a coupling clip (18) which locks the gun body (1) frictionally with the housing cover (5) as the housing cover (5) is closed.

3. The two-plunger mixing gun according to claim 1, wherein housing cover (5) is pivotally mounted on the receiving shaft (4) by hinges (9).

4. The two-plunger mixing gun according to claim 1, wherein the cartridges (22) are provided with pierceable termination films.

5. The two-plunger mixing gun according to claim 1, wherein the cartridges (22) are laminated on their inside with a film resistant to the individual components of two-component molding composition.

\* \* \* \* \*